United States Patent [19]
Dookhith et al.

[11] Patent Number: 5,254,344
[45] Date of Patent: * Oct. 19, 1993

[54] OIL-IN-WATER PESTICIDAL EMULSION, PROCESS FOR APPLICATION

[75] Inventors: Mohammad Dookhith, Thurins; Hubert Linares, Caluire, both of France

[73] Assignee: Rhone-Poulenc Inc., Research Triangle Park, N.C.

[*] Notice: The portion of the term of this patent subsequent to Mar. 17, 2009 has been disclaimed.

[21] Appl. No.: 850,943

[22] Filed: Mar. 13, 1992

Related U.S. Application Data

[63] Continuation of Ser. No. 526,776, May 17, 1990, Pat. No. 5,096,711, which is a continuation of Ser. No. 343,043, Apr. 25, 1989, abandoned.

[30] Foreign Application Priority Data

May 9, 1988 [FR] France ............... 88 06494

[51] Int. Cl.$^5$ ............................................. A01N 25/00
[52] U.S. Cl. ........................... 424/405; 71/DIG. 1; 252/106; 514/938
[58] Field of Search ............ 424/405; 71/DIG. 1; 252/106; 514/938; 423/608, 610

[56] References Cited

U.S. PATENT DOCUMENTS

| | | | |
|---|---|---|---|
| 3,317,305 | 5/1967 | Stefcik | 514/772 |
| 3,873,689 | 3/1975 | Frensch et al. | 514/772.4 |
| 3,888,684 | 6/1975 | Little | 106/15 AF |
| 3,948,636 | 4/1976 | Marks | 71/DIG. 1 |
| 3,988,294 | 10/1976 | Hill | 514/596 X |
| 4,188,202 | 2/1980 | Gillings et al. | 71/DIG. 1 |
| 4,313,847 | 2/1982 | Chasin et al. | 71/DIG. 1 |
| 4,372,943 | 2/1983 | Papanu et al. | 424/78 |
| 4,411,692 | 10/1983 | LeClair et al. | 71/DIG. 1 |
| 4,493,725 | 1/1985 | Moon et al. | 71/62 |
| 4,556,426 | 12/1985 | Chesney, Jr. et al. | 106/18.32 |
| 4,594,096 | 6/1986 | Albrecht et al. | 514/256 |
| 4,626,274 | 12/1986 | Hausmann et al. | 71/90 X |
| 4,678,503 | 7/1987 | Barlet et al. | 71/DIG. 1 |
| 4,725,589 | 2/1988 | Tsuboi et al. | 514/256 |
| 4,795,640 | 1/1989 | Helfenberger | 424/405 |
| 4,810,279 | 3/1989 | Martin | 71/121 |
| 4,818,536 | 4/1989 | Meyers et al. | 514/938 |
| 4,822,405 | 4/1989 | Martin et al. | 71/DIG. 1 |
| 4,828,835 | 5/1989 | Meyers et al. | 514/938 |
| 4,853,026 | 8/1989 | Frisch et al. | 71/86 |
| 5,049,309 | 9/1991 | Sakamoto et al. | 252/313.1 |

FOREIGN PATENT DOCUMENTS

| | | |
|---|---|---|
| 070702 | 1/1983 | European Pat. Off. |
| 289909 | 11/1988 | European Pat. Off. |
| 2804141 | 8/1978 | Fed. Rep. of Germany |
| 3004010 | 8/1980 | Fed. Rep. of Germany |
| 3005016 | 8/1980 | Fed. Rep. of Germany |
| 3304457 | 6/1983 | Fed. Rep. of Germany |
| 2552627 | 4/1985 | France |
| 48-008922 | 2/1973 | Japan |
| 50-018242 | 2/1975 | Japan |
| 53-145914 | 12/1978 | Japan |
| 55-020750 | 2/1980 | Japan |
| 56-086105 | 7/1981 | Japan |
| 56-152401 | 11/1981 | Japan |
| 58-177902 | 10/1983 | Japan |
| 59-199602 | 11/1984 | Japan |
| 60-146808 | 8/1985 | Japan |
| 62-004210 | 1/1987 | Japan |
| 83/002939 | 9/1983 | PCT Int'l Appl. |
| 2022418 | 12/1979 | United Kingdom |
| 2082914 | 3/1982 | United Kingdom |
| 2113116 | 8/1983 | United Kingdom |

Primary Examiner—Thurman K. Page
Assistant Examiner—Robert H. Harrison
Attorney, Agent, or Firm—James G. Passé

[57] ABSTRACT

The present invention relates to an oil-in-water pesticidal emulsion comprising a lipophilic pesticidal substance, optionally an organic solvent dissolving the said substance, water and an emulsifying system capable of ensuring the dispersion of the oily phase in the aqueous phase, wherein the said emulsion additionally comprises a dispersing agent based on titanium dioxide. The present invention also comprises a suspoemulsion obtained by adding a solid pesticide to the above-mentioned emulsion followed by milling.

4 Claims, No Drawings

OIL-IN-WATER PESTICIDAL EMULSION, PROCESS FOR APPLICATION

This application is a continuation of application Ser. No. 526,776 filed May 17, 1990, now U.S. Pat. No. 5,096,711; which is a continuation of application Ser. No. 343,043 filed Apr. 25, 1989, now abandoned.

The present invention relates to a concentrated emulsion of the oil-in-water type exhibiting a pesticidal activity and to a process for making use of the said emulsion. It also relates to a suspoemulsion obtained by milling the said emulsion with an additional solid pesticidal substance.

In general, an emulsion is the result of dispersing one immiscible liquid in another, and is made relatively stable by means of one or more emulsifying agents, also known as a surfactant.

In the general case of emulsions for pesticidal use the dispersed oily phase is made up of a lipophilic pesticidal substance in combination with one or more solvents in the case where this lipophilic substance is naturally in the solid state at the temperature or in the temperature region under consideration, whereas the dispersing phase consists of water and of various other additives, the surface-active agent(s) being responsible for the interface between the two phases.

Nevertheless, this basic outline is far from enabling the person skilled in the art to solve all the problems linked with the production of such emulsions in the case of each pesticide.

It is known, in fact, that preformed emulsions of pesticidal lipophilic substances in aqueous media tend to break when, as a result of a temperature variation, these substances change from the solid state into the liquid state, to return into the solid state (solidifying/melting).

This disadvantage is particularly detrimental when the melting point of such pesticidal substances is in the range of temperature variation within which the said substance is stored, because this makes the composition unsuitable for later use.

Thus, an aim of the present invention is to propose an oil-in-water emulsion exhibiting great stability.

Another aim of the present invention is to stabilize oil-in-water emulsions based on pesticidal substances or on a mixture of pesticidal substances whose melting point is within the range of variation of storage temperature of the said substances.

Similarly, it is known that in the case of pesticidal products which have a melting point below 100° C. it is very difficult to produce an aqueous suspension, because they begin to change state well before their melting point, and this consequently makes them difficult to mill. This is the case especially in hot countries, or in the summer in temperate regions.

The present invention consequently makes it possible to provide stable compositions in a liquid form with compounds which have a melting point below 100° C.

Another aim of the present invention is therefore to provide liquid, stable, improved compositions with pesticidal products which have a melting point below 100° C.

Thus, in its most general form, the invention relates to a pesticidal emulsion of the oil-in-water type, comprising:

a lipophilic pesticidal substance, optionally an organic solvent dissolving the said substance, water and an emulsifying system capable of ensuring the dispersion of the oily phase in the aqueous phase, wherein the said emulsion additionally comprises a dispersing agent based on titanium dioxide.

The invention preferably relates to a pesticidal emulsion of the oil-in-water type comprising: a lipophilic pesticidal substance which has a melting point below 100° C., optionally an organic solvent dissolving the said substance, water and an emulsifying system capable of ensuring the dispersion of the oily phase in the aqueous phase, wherein the said emulsion additionally comprises a dispersing agent which is based on titanium dioxide.

Also preferably, the invention relates to a pesticidal emulsion of the oil-in-water type comprising: a lipophilic pesticidal substance which has a melting point situated within the range of temperature variation to which the said substance is subjected, especially during storage, optionally an organic solvent dissolving the said substance, water and an emulsifying system capable of ensuring the dispersion of the oily phase in the aqueous phase, wherein the said emulsion additionally comprises a dispersing agent based on titanium dioxide.

The range within which the temperatures can vary during storage is usually between $-20°$ and $+60°$ C. Exceptional conditions may, of course, extend above or below the range defined above, but it should be understood that the formulations according to one of the preferred alternative forms of the invention can be used in all the cases where the temperature variation causes a change of state in the pesticide.

A pesticide means either an active substance or a mixture, for example binary or ternary, of an active substance. These mixtures may exhibit a eutectic point, well known in physical chemistry. Also, in the case of these mixtures, the invention will preferably relate to those whose eutectic point is below 100° C. or those whose eutectic point is situated within the temperature variation region, as defined above. Furthermore, however, the invention also relates to mixtures without a eutectic point, in which at least one of the substances corresponds to the above definition.

Pesticidal substances are numerous and diverse and it is not part of the applicant's intention to limit the invention to any category of pesticide whatever, except that, in the case of one of the preferred alternative forms of the invention, they must meet the criteria defined above, namely have a melting point below 100° C. or a melting point within the region of temperature variation as indicated above.

Insecticides, fungicides, herbicides, nematicides, rodenticides and repellent products may be mentioned, no limitation being implied.

Among these there may be mentioned phosalone, the aclonifen-oxadiazon mixture, aclonifen-linuron, aclonifen-bifenox, bifenox, acephate, aclonifen, alachlor, aldicarb, amethryn, aminocarb, amitraz, azamethiphos, azinphos-ethyl, azinphos-methyl, aziprotryne, benolaxyl, benfluralin, bensulide, bensultap, benzoximate, benzoyl-prop-ethyl, bifenthrin, binopacryl, bromophos, bromopropylate, bromoxynil esters, bupirimate, buthiobate, butocarboxim, carboxin, chlorbufam, chlordimeform, chlorfenson, chlormephos, chlorobenzilate, flurochloridone, chloropropylate, chlorphoxim, chlorpropham, chlorpyrifos, chlorpyrifos-methyl, cloethocarb, cyanophos, cycloate, cycloxydim, cyfluthrin, demethon-S-methyl, desmetryn, dialifos, diazinon, diclofop, dicofol, diethatyl, dimethachlor, dimethomethryn, dimethoate dinobuton, dinoseb, dioxabenzofos, DNOC (2-methyl-4,6-dinitrophenol), EPN (O-ethyl O-(4-nitrophenyl)phenylphosphonothioate etaconazole, ethalfluralin, ethiofencarb, ethofumesate, famphur, fenamiphos, fenitropan, fenobucarb, fenothiocarb, fenoxaprop, fenoxycarb, fenpropathrin, fenson, flanuprop, fluchloralin, fluorodifen, fluoroglycofen, flurecol, fluroxypyr, formothion, furolaxyl, furmecyclox, haloxyfop, heptenophos, hymexazol, iodofenphos, ioxynil esters, isoprothiolane, linuron, metalaxyl, metazachlor, methamidophos, methidathion, methopotryne, metolcarb, monalide, monocrotophos, monolinuron, myclobutanil, napropamide, nitrapyrin, nitrofen, nitrothalisopropyl, oxabetrinil, oxadiazon, oxyfluorfen, parathion-methyl, penconazole, pendimethalin, pentanochlor, phenthoate, phosfolan, phosmet, piproctanil, pirimicarb, prochloraz, profluralin, promecarb, prometon, propachlor, propdmocarb, propanil, propetamphos, propham, propoxur, propthoate, pyrazophos, pyridate, quinalphos, quizalofop, resmethrin, secbumeton, simetryn, tebutan, tefluthrin, temephos, tetramethrin, tetrasul, thiofanox, tolclofos-methyl, triadimefon, trichlorfon, tridiphane, triflumizole, trifluralin, and xylylcarb.

The invention has been found to be particularly advantageous in the case of bromoxynil esters, especially bromoxynil $C_1$–$C_8$ alkanoates by themselves or mixed, such as bromoxynil butanoate, heptanoate and octanoate, which are compounds that are well known in the art.

The concentration of bromoxynil ester will advantageously vary between 100 g/l and 600 g/l, based on bromoxynil phenol, depending on the esters or ester mixtures employed.

If the lipophilic organic substance requires it, which is usually the case, it is dissolved in a suitable organic solvent. Within the scope of the present invention, the term solvent covers both a single solvent and a mixture of several solvents. The particular organic solvent is obviously not critical and any solvent or solvent mixture whatever may be employed.

Among solvents there may be mentioned commercial solvents of aromatic/paraffinic nature, such as solvessos or kerosenes, or solvents of an alkylaromatic, aliphatic or cycloaliphatic type, or else natural vegetable oils such as rape oil or modified oils.

There may also be mentioned alcohols such as cyclohexanol, ketones such as cyclohexanone and acetophenone, chlorinated solvents such as carbon tetrachloride or chloroform, dimethylformamide and dimethyl sulphoxide.

It is generally preferable to employ a pair of solvents, one being rather hydrophobic, such as the hydrocarbon solvents mentioned above, and the other being rather hydrophilic, such as the solvents containing functional groups referred to above, the balance between the hydrophobic solvent and the hydrophilic solvent being obviously a function of the nature of the pesticide or of the pesticide mixture.

Among the surfactants, particular mention will be made of nonionic surfactants which are the result of reaction of at least one mole of alkylene oxide, especially propylene oxide or ethylene oxide, with an organic compound containing at least six carbon atoms and one active hydrogen atom. These organic compounds include phenols and aliphatic alcohols, mercapto compounds such as dodecyl mercaptan, oleyl mercaptan and cetyl mercaptan, thiophenols and thionaphthols, carboxylic acid amides, sulphonamides, and compounds called Pluronics, as described in U.S. Pat. No. 2,674,619.

It is generally desirable to employ products containing at most 30 moles of alkylene oxide (especially ethylene oxide) per residue of the abovementioned organic compound.

Among the surfactants referred to above, preference will be given to:

the products of addition of ethylene oxide to an alkylphenol. The alkylphenols contain one or more alkyl radicals attached to the phenol nucleus, the total number of carbon atoms in the alkyl chain(s) ranging from 7 to 24, the preferred alkylphenols being those which contain 1 or 2 alkyl groups, each containing 7 to 12 carbon atoms. These alkylphenols also include the methylenephenols obtained, for example, by condensing phenols with formaldehyde.

A particularly advantageous example is the product of condensation of 1 to 20 ethylene oxide units with nonylphenol;

products of addition of ethylene oxide to a condensation product obtained by attaching compounds containing phenolic hydroxyl groups to compounds containing olefinic double bonds and carbon rings.

The following may be mentioned as representing such condensation products: mono (1-phenylethyl) phenol, di(1-phenylethyl)phenol, tri(1-phenylethyl)phenol, diphenylisopropyl phenol, mono(1-phenylethyl)-cresol, (1-phenylethyl)naphthol and dicyclohexylphenol.

It will be noted that the 1-phenylethyl functional group is commonly called the styryl functional group.

The condensation products may be subjected to the alkoxylation in the form of single bodies, but it is also possible to employ them in the form of mixtures, such as are commonly obtained in the addition by linking.

Among these, preference will be given to mono- or di- or tri(1-phenylethyl)phenols or, more commonly called, styrylphenols.

All these surfactants are well known to a person skilled in the art.

By way of example, reference can usefully be made to French Patent No. 1,395,059, granted on Mar. 1, 1965, no limitation being implied.

Nevertheless, within the scope of the present invention, it is preferred to choose an emulsifying system made up of two nonionic surface-active agents, one having hydrophilic properties and the other lipophilic properties.

Thus, among the surface-active agents referred to above there will be chosen, in the case of the hydrophilic agents, those which contain at least 7 alkylene oxide units; whereas surface-active agents containing fewer than 7 alkylene oxide units will be chosen in the case of lipophilic surface-active agents.

It is known that natural titanium dioxide crystallizes in three allotropic varieties:rutile, anatase and brookite. These three varieties are suitable within the scope of the present invention.

Titanium oxide is manufactured by the French company Thann et Mulhouse.

The oil-in-water emulsion will advantageously comprise, in grams/liter:

| | | |
|---|---|---|
| lipophilic pesticidal substance | 100 to 800 | oily phase |
| solvent | 0 to 350 | |
| hydrophobic surface-active emulsifying agent | 0 to 100 | |
| hydrophilic surface-active emulsifying | 20 to 60 | |

-continued

| agent | |
|---|---|
| water balance to | 1,000 |
| and a titanium dioxide-based dispersing or stabilizing agent. | |

This dispersing agent is preferably present in a proportion of 1 g/l to 100 g/l of emulsion, advantageously 5 g/l to 50 g/l.

It has been found, quite unexpectedly, that the addition of this dispersing agent greatly improved the stability of oil-in-water emulsions.

In addition to this basic composition, it is advantageous to incorporate an anionic surfactant like sulphonic acids, such as long-chain alkylbenzenesulphonates, optionally in the form of amine or ammonium salts. For example, ammonium dodecylbenzenesulphonate will advantageously be employed. With reference to the composition described above, between 0 and 10 g/liter, preferably 2 to 10 g/liter of anionic surfactant will preferably be employed.

In order to lower the solidification point of the suspension and, consequently, to promote the pourability of the composition, it is also possible to incorporate one or more plasticizing diols such as ethylene glycol, propylene glycol, glycerol or di- or tri- or tetraethylene glycol, in a quantity which usually varies between 0 and 50 g/l, with reference to the composition defined above.

It is also possible to incorporate in the compositions according to the invention all kinds of other ingredients and especially antifoam agents such as a silicone oil (silicone oil-silica mixture), certain alcohols or phenols which have few ethoxy units, biocidal agents such as citric, propionic and benzoic acids, or their salts or esters, in a quantity which usually varies between 0 and 50 g/l with reference to the composition defined above.

In addition to the abovementioned constituents, the compositions according to the invention may contain up to 50 g/l of thickeners. Thickeners are products which, when added to the emulsions according to the invention, impart pseudoplasticity properties to them. The thickeners which may be employed in the invention may be inorganic and/or organic in nature.

As a thickener of inorganic type there may be mentioned attapulgites, bentonites, caponites and colloidal silicas.

As a thickener of organic type there may be mentioned hydrophilic biopolymers of the heteropolysaccharide type of a thickening character, water-soluble polymers such as celluloses, methyl cellulose and acrylic derivatives, and vinylpyrrolidone.

The hydrophilic biopolymers of the heteropolysaccharide type which may be employed in the invention are known products. They have a molecular weight higher than 200,000 and preferably higher than 1,000,000; they have pseudoplasticity properties and are generally obtained by the action (i.e. by fermentation) of bacteria of the genus Xanthomonas on carbohydrates. These biopolymers are also sometimes referred to by a variety of other expressions such as: Xanthomonas hydrophilic colloids, heteropolysaccharide resins, xanthan resins, extracellular heteropolysaccharides originating from Xanthomonas or from bacteria of the Pseudomonadaceae family. The word biopolymer is employed to mean that a polymer originating from a biological process (bacterial fermentation in this case) is involved.

The bacteria employed for the preparation of these biopolymers are in most cases *Xanthomonas campestris*, but it is also possible to employ other Xanthomonas such as *Xanthomonas carotae, Xanthomonas incanae, Xanthomonas begoniae, Xanthomonas malvacearum, Xanthomonas vesicatoria, Xanthomonas translucens* or *Xanthomonas vasculorum*. Suitable carbohydrates for fermentation with the aid of suitable carbons for the fermentation, with the aid of Xanthomonas bacteria are glucose, sucrose, fructose, maltose, lactose, galactose, starch, potato starch, etc.

The above oil-in-water concentrated emulsions may be prepared by any convenient method, but are preferably prepared by the combination of the hydrophobic nonionic surface-active agent with a mixture of the solvent and of the lipophilic pesticide and then the combination of the resulting three-constituent mixture with the aqueous phase containing the hydrophilic surfactant and the dispersing agent, this last stage being accompanied by stirring to form the emulsion. An emulsion of more mediocre quality is obtained when the nonionic surface-active agent(s) (emulsifiers) are added to the aqueous phase in the emulsion-forming step.

The addition may also be performed using a reverse method. This means placing the oily phase in the aqueous phase and this is an additional advantage of titanium dioxide. The emulsion obtained is next homogenized by various methods.

Thus, one method consists of employing an efficient disperser or a bead mill or a colloid mill or an APV Gaulin-type plunger homogenizer to obtain a droplet size of sufficiently fine diameter (median diameter of between 0.5 and 1 micron).

The pesticidal emulsions according to the invention are used by dilution with water so as to obtain the effective pesticidal concentration.

As already briefly mentioned in the preamble of the description, emulsions such as just described can lead to excellent suspoemiilsions by addition of a solid pesticidal substance which is then milled by means of a mill.

These suspoemulsions are especially useful in the case of mixtures with carbaryl or thiodicarb.

The examples below containing the following lipophilic pesticidal substances identified by common name and chemical name illustrate the invention:

| | |
|---|---|
| aclonifen | 2-chloro-6-nitro-3-phenoxy-benzenamine; |
| alachlor: | α-chloro-2',6'-diethyl-N-methoxymethylacetanilide; |
| bifenox | methyl 5-(2,4-dichloro-phenoxy)-2-nitrobenzoate; |
| bromoxynil octanoate | 2,6-dibromo-4-cyanophenyl octanoate; |
| bromoxynil heptanoate | 2,6-dibromo-4-cyanophenyl heptanoate; |
| carbaryl | 1-naphthalene methyl-carbamate; |
| ethion | S,S'-methylene-bis-(O,O-diethylphosphorodithioate; |
| ethoprophos | O-ethyl-S,S-dipropyl-phosphorodithioate; |
| linuron | N'-(3,4-dichlorophenyl)-N-methoxy-N-methylurea; |
| oxadiazon | 5-t-butyl-3-(2,4-dichloro-5-isopropoxyphenyl)-1,3,4-oxadiazol-2(3H)-one; |
| phosalone | 6-chloro-3-diethoxyphosphino-thioylthiomethyl-1,3-benzoxazol-2(3H)-one; and |
| thiodicarb | N,N'-[thiobis[(methylimino)-carbonyloxy]bis[ethanimido-thioate]. |

EXAMPLE 1

A homogeneous oily mixture is obtained by mixing in a container, with stirring, phoslone (350 g), acetophenone (200 g), solvesso 200 (50 g) and a nonylphenolethylene oxide polycondensate (1 EO; 50 g).

Similarly, by mixing in another container, with stirring and while heating to about 40° C., water (390 cc), an ethylene oxide-propylene oxide condensate (EO:PO 70:30; 40 g), melted beforehand, a dodecylbenzenesulphonate amine salt (4 g), propylene glycol (20 g), attapulgite (12 g), titanium dioxide in anatase form (12 g), and antifoam (2 g), a homogeneous aqueous dispersion is obtained.

The oily mixture is then run into the aqueous mixture in a well-stirred vessel and is made up to 1:1 by adding water if necessary. This mixture is then homogenized by being passed through a bead mill (1-mm glass beads).

The emulsion obtained has the following composition (in g/l):

| | | |
|---|---|---|
| phosalone | 350 | oily phase |
| acetophenone | 200 | |
| SOLVESSO 200 | 50 | |
| 1:1 ethylene oxide/nonylphenol condensate | 50 | |
| propylene oxide/ethylene oxide condensate (EO:PO 70:30) | 40 | |
| dodecylbenzenesulphonate amine salt | 4 | |
| propylene glycol | 20 | |
| attapulgite | 12 | |
| titanium dioxide in anatase form | 12 | |
| antifoam | 2 | |
| balance water up to 1 liter | | |

The following examples were produced using the same method.

EXAMPLE 2

The following emulsion was produced (in g/l):

| | | |
|---|---|---|
| oxadiazon | 100 | oily phase |
| aclonifen | 300 | |
| acetophenone | 300 | |
| 1:1 ethylene oxide/nonylphenol condensate (1 EO) | 50 | |
| propylene oxide/ethylene oxide condensate (EO:PO 70:30) | 34 | |
| dodecylbenzenesulphonate amine salt | 3.4 | |
| propylene glycol | 17 | |
| attapulgite | 10 | |
| titanium dioxide in anatase form | 10 | |
| antifoam | 1.7 | |
| balance water up to 1 liter | | |

EXAMPLE 3

The following emulsion was produced (in g/l):

| | | |
|---|---|---|
| linuron | 83 | oily phase |
| aclonifen | 250 | |
| acetophenone | 350 | |
| 1:1 ethylene oxide/nonylphenol condensate (1 EO) | 20 | |
| propylene oxide/ethylene oxide condensate (EO:PO 70:30) | 35 | |
| dodecylbenzenesulphonate amine salt | 3.5 | |
| propylene glycol | 19 | |
| attapulgite | 10 | |
| titanium dioxide in anatase form | 10 | |
| antifoam | 2 | |
| balance water up to 1 liter | | |

EXAMPLE 4

The following emulsion was produced (in g/l):

| | | |
|---|---|---|
| bifenox | 105 | oily phase |
| aclonifen | 311 | |
| acetophenone | 330 | |
| 1:1 ethylene oxide/nonylphenol condensate (1 EO) | 50 | |
| propylene oxide/ethylene oxide condensate (EO:PO 70:30) | 35 | |
| dodecylbenzenesulphonate amine salt | 4 | |
| propylene glycol | 20 | |
| attapulgite | 12 | |
| titanium dioxide in anatase form | 12 | |
| anitfoam | 2 | |
| balance water up to 1 liter | | |

EXAMPLE 5

| | | |
|---|---|---|
| phosalone | 450 | oily phase |
| acetophenone | 200 | |
| SOLVESSO 200 | 100 | |
| propylene oxide/ethylene oxide condensate (EO:PO 70:30) | 34 | |
| dodecylbenzenesulphonate amine salt | 3 | |
| propylene glycol | 17 | |
| attapulgite | 10 | |
| titanium dioxide in anatase form | 10 | |
| antifoam | 2 | |
| balance water up to 1 liter | | |

EXAMPLE 6

The following emulsion was produced (in g/l):

| | | |
|---|---|---|
| alachlor | 180 | oil phase |
| aclonifen | 210 | |
| acetophenone | 200 | |
| SOLVESSO 200 | 50 | |
| 2:1 ethylene oxide/nonylphenol condensate | 50 | |
| propylene oxide/ethylene oxide condensate (EO:PO 70:30) | 34 | |
| dodecylbenzenesulphonate amine salt | 4 | |
| propylene glycol | 20 | |
| attapulgite | 12 | |
| titanium dioxide in rutile form | 12 | |
| antifoam | 2 | |
| balance water up to 1 liter | | |

EXAMPLE 7

The following emulsion was produced (in g/l):

| | | |
|---|---|---|
| alachlor | 143 | oily phase |
| aclonifen | 257 | |
| acetopheneone | 150 | |
| SOLVESSO 200 | 50 | |
| propylene oxide/ethylene oxide condensate (EO:PO 70:30) | 47 | |
| dodecylbenzenesulphonate amine salt | 4.7 | |
| propylene glycol | 24 | |
| attapulgite | 14 | |

-continued

| | |
|---|---|
| titanium dioxide in anatase form | 14 |
| antifoam | 2.4 |
| hydroxypropylcellulose | 1 |
| balance water up to 1 liter | |

EXAMPLE 8

| | | |
|---|---|---|
| ethoprofos | 400 | ⎫ |
| acetophenone | 50 | ⎬ oily phase |
| propylene oxide/ethylene oxide condensate (EO:PO 70:30) | 60 | ⎭ |
| dodecylbenzenesulphonate amine salt | 6 | |
| propylene glycol | 30 | |
| attapulgite | 17 | |
| titanium dioxide in rutile form | 17 | |
| antifoam | 3 | |
| colorant | 0.1 | |
| balance water up to 1 liter | | |

The following examples were produced using the same method.

EXAMPLE 9

The following emulsion was produced (in g/l):

| | | | |
|---|---|---|---|
| bromoxynil octanoate | 112.5 | based on | ⎫ |
| bromoxynil heptanoate | 112.5 | bromoxynil | ⎬ oil phase |
| SOLVESSO 200 | 100 | phenol | ⎭ |
| propylene oxide/ethylene oxide condensate (EO:PO 70:30) | 60 | | |
| dodecylbenzenesulphonate amine salt | 6 | | |
| propylene glycol | 30 | | |
| attapulgite | 20 | | |
| titanium dioxide in anatase form | 20 | | |
| hydroxypropyl cellulose | 2 | | |
| balance water up to 1 liter | | | |

EXAMPLE 10

The following emulsion was produced (in g/l):

| | | | |
|---|---|---|---|
| bromoxynil octanoate | 112.5 | based on | ⎫ |
| bromoxynil heptanoate | 112.5 | bromoxynil | ⎬ oily phase |
| esterified rape oil | 50 | phenol | ⎭ |
| propylene oxide/ethylene oxide condensate (EO:PO 70:30) | 60 | | |
| dodecylbenzenesulphonate amine salt | 6 | | |
| propylene glycol | 30 | | |
| attapulgite | 20 | | |
| titanium dioxide in anatase form | 20 | | |
| hydroxypropyl cellulose | 2 | | |
| balance water up to 1 liter | | | |

EXAMPLE 11

The following suspoemulsion was produced (in g/l) technical thiodicarb (92%, 163 g), oily phase is dispersed with stirring in a mixture containing:

| | |
|---|---|
| 7:1 ethylene oxide/polyarylphenol sulphate condensate (7 EO) | 25 |
| complex phosphoric ester | 25 |
| ethylene oxide/nonylphenol condensate with 2, 7 and 10 EO | 80 |
| deodorizer | 10 |
| attapulgite | 20 |
| titanium dioxide in anatase form | 20 |
| antifoam | 5 |
| balance water up to 1 liter | |

A dispersion of solid in water is therefore obtained. Technical ethion (96%; 391 g) is then added and a homogeneous suspoemulsion is obtained, which iB milled in a bead mill.

EXAMPLE 12

The following suspoemulsion was produced (in g/l) under the same conditions as above:

| | | |
|---|---|---|
| technical ethion, 96% | 261 | ⎫ oily phase |
| technical carbaryl, 92% | 229 | ⎭ |
| 7:1 ethylene oxide/polyarylphenol sulphate polycondensate (7 EO) | 50 | |
| ethylene oxide/nonylphenol polycondensate with 2, 7 and 10 EO | 85 | |
| deodorizer | 10 | |
| attapulgite | 15 | |
| titanium dioxide in anatase form | 30 | |
| balance water up to 1 liter | | |

Example 13—Stability test

The compositions were then subjected to various stability tests:

Firstly, these compositions are subjected to five cycles of uniform temperature variations during five weeks from −10° C. to 35° C.

Secondly, these compositions are placed for one month in an oven at 50° C.

Thirdly, these compositions are placed at 35° C for three months.

It is found that these compositions exhibit no phase separation or flocculation phenomena at the end of these three tests.

COMPARATIVE TEST

By way of a comparative example, an emulsion was produced according to Example 2, but leaving out titanium dioxide.

On being treated as shown above for 1 month at 50° C, this emulsion separated into two phases which were not reversible by stirring, making it unsuitable for use.

We claim:

1. A stabilized oil-in-water pesticidal emulsion comprising:
   a pesticidally effective amount of a lipophilic substance which has a melting point below 100° C. and is optionally dissolved in an organic solvent;
   water;
   an emulsifying system consisting of an effective oil in water emulsifying amount of at least one surface active agent; and
   a titanium dioxide dispersing or stabilizing agent in an amount, and of a particle size, effective to maintain or improve the stability of the emulsion.

2. The stabilized oil-in-water pesticidal emulsion of claim 1, wherein the lipophilic pesticidal substance has a melting point situated within the range of temperature variation to which said substance is subjected during storage.

3. The emulsion according to claim 1 or 2, wherein the titanium dioxide is present in a proportion of 1 g/l to 100 g/l of emulsion.

4. The emulsion according to claim 3, wherein the titanium dioxide is present in a proportion of 5 g/l to 50 g/l of emulsion.

* * * * *